US00PP19938P2

(12) United States Plant Patent
van Noort

(10) Patent No.: US PP19,938 P2
(45) Date of Patent: Apr. 21, 2009

(54) ***BERGENIA* PLANT NAMED 'SOLAR FLARE'**

(50) Latin Name: *Bergenia*
Varietal Denomination: Solar Flare

(76) Inventor: Marco van Noort, c/o Marco van Noort Vaste Planten, Wasbeeklaan 13, Warmond (NL), 2361 HG ( * ) Notice: Subject to any disclaimer, the term of this patent is extended or adjusted under 35 U.S.C. 154(b) by 0 days.

(21) Appl. No.: 11/982,270

(22) Filed: Oct. 31, 2007

(51) Int. Cl.
*A01H 5/00* (2006.01)

(52) U.S. Cl. ..... Plt./409
(58) Field of Classification Search ..... Plt./409
See application file for complete search history.

*Primary Examiner*—Wendy C Haas
(74) *Attorney, Agent, or Firm*—Klarquist Sparkman, LLP

(57) ABSTRACT

A new and distinct *Bergenia* plant characterized by foliage with a broad, yellow, variegated margin on new growth, large, bright pink flowers, red winter leaf color, and excellent vigor.

1 Drawing Sheet

Botanical denomination: *Bergenia* spp.
Variety designation: 'Solar Flare'.

BACKGROUND OF THE INVENTION

The present invention relates to a new and distinct *Bergenia* hybrid and given the cultivar name of 'Solar Flare'. *Bergenia* is in the family *Saxifragaceae*. The new cultivar originated as a branch mutation in tissue cultured plants of *Bergenia* 'Herbstblute' (unpatented). This mutant has proved stable since it was discovered in September of 2003.

SUMMARY OF THE INVENTION

This new *Bergenia* is distinguished by:

1. Foliage with a broad yellow variegated margin on new growth;
2. Large, bright pink flowers;
3. Red winter leaf color; and
4. Excellent vigor.

Compared to the parent, the new cultivar has a yellow variegated margin rather than not variegated. There are no other yellow variegated margined *Bergenia* on the market known to the inventor. This new cultivar has been reproduced only by asexual propagation (division and tissue culture). Each of the progeny exhibits identical characteristics to the original plant. Asexual propagation by tissue culture using standard micropropagation techniques with terminal shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
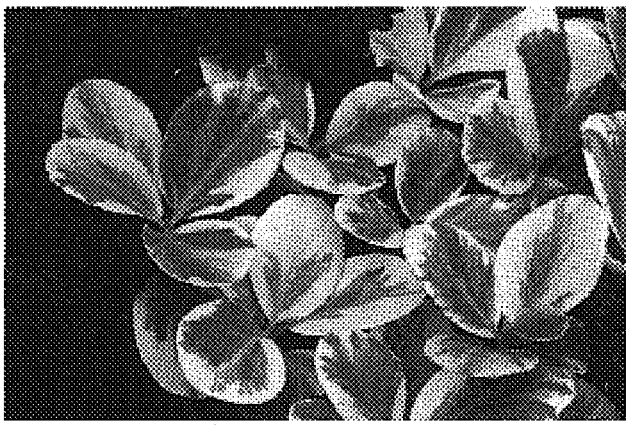
FIG. 1 shows a young *Bergenia* 'Solar Flare' plant.
Figure 2:
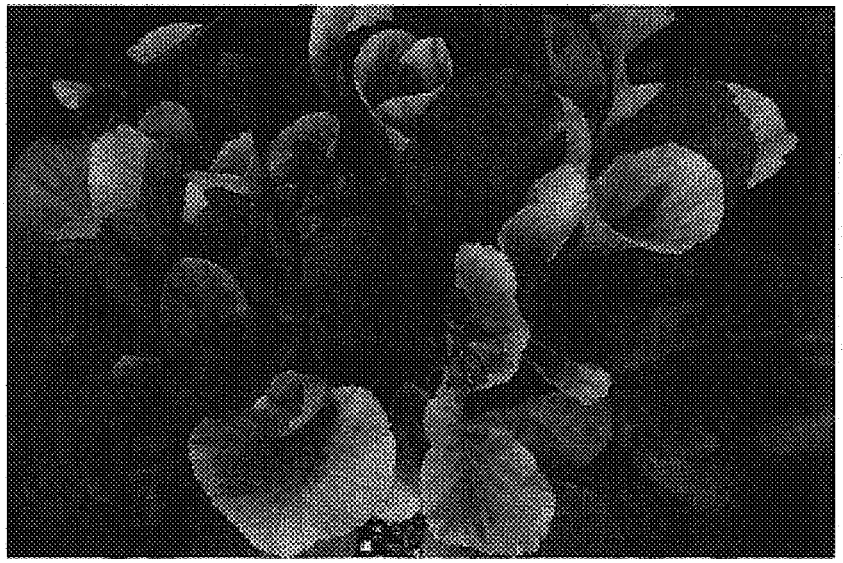
FIG. 2 shows the flowers, foliage, and habit of a two-year old *Bergenia* 'Solar Flare' in March in Canby, Oreg.
Figure 3:
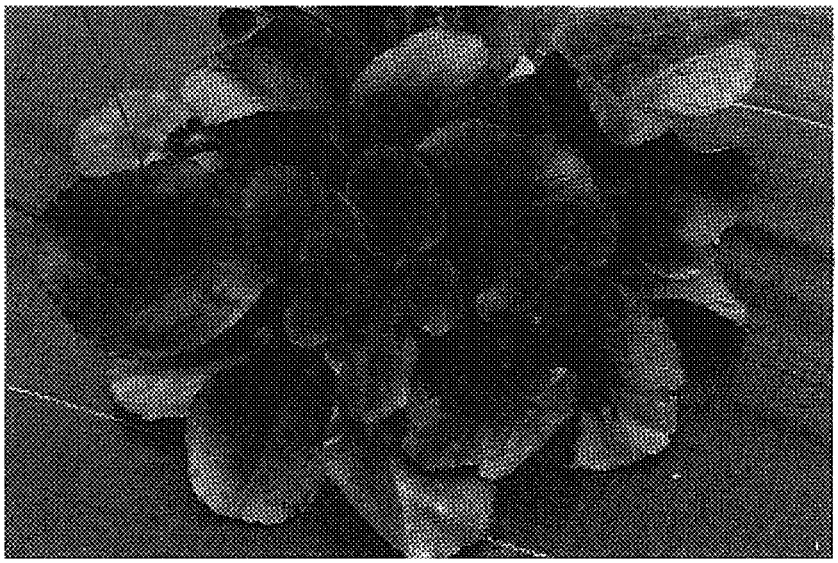
FIG. 3 shows a one year old *Bergenia* 'Solar Flare' in the field in late February showing winter color.

The following is a detailed description of the new *Bergenia* based on observations of two-year-old specimens grown in the ground in full sun in the trial fields in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on the Royal Horticultural Society Colour Chart.

Plant:
- *Type.*—Herbaceous perennial.
- *Hardiness.*—USDA Zones 3 to 9.
- *Size.*—45 cm wide and 27 cm tall.
- *Form.*—Clumping.
- *Vigor.*—Excellent.
- *Roots.*—Fibrous network, White 155A.

Leaf:
- *Number.*—About 10 over wintering per crown, each crown with 2 new spring crowns; about 10 main crowns per plant.
- *Type.*—Simple.
- *Shape.*—Obovate.
- *Arrangement.*—Rosette.
- *Blade size.*—Grows to 13 cm long and 10.5 cm wide.
- *Margins.*—Dentate.
- *Apex.*—Obtuse to subacute.
- *Base.*—Obtuse.
- *Venation.*—Pinnate.
- *Surface texture.*—Glabrous on both surfaces.
- *Petiole description.*—Grows to 8.5 cm long and 1 cm wide, glabrous, base sheathing, sheath ligulate and spreading to 3 cm wide at base, Yellow Green 145B overall in spring to Yellow — Green 146D with red backs, Greyed Red 182A.
- *Color.*—Topside spring — center irregularly blotched medium to light green, Yellow Green 147B and 147C surrounded by a yellow margin Yellow 3C, bottom side is Yellow 146A in the center and edges Green Yellow 1C; summer leaves are deep green, Green 137A on top and Yellow Green 146C heavily tinted Greyed Red 185A on the bottom side; winter leaves topside — between Greyed Purple 187B and Brown 200B, bottom side Yellow Green 146C heavily tinted Greyed Red 185A.

Inflorescence:

*Type.*—Scapose cyme.

*Number of flowers per scape.*—18.

*Peduncle.*—Grows to 24 cm tall and 9 cm wide, glandular near top, Yellow Green 150D at the base to Yellow Green 146D in shade and Red Purple 185A where in sun.

*Pedicel.*—Grows to 1 cm long, 2 mm wide, glandular, Greyed Red 185A.

Flower bud:

*Size.*—15 mm long and 10 mm wide.

*Shape.*—Ovoid.

*Color.*—Red Purple 71B at the tip where the petals show and Greyed Purple 183B where sepals show.

Flower:

*Type.*—Bisexual, side or down facing at first.

*Size overall.*—2 cm long and 1.5 cm wide.

*Corolla description.*—Overall size 1.3 cm deep and 1.5 cm wide, glabrous inside and out; petals, 5 in number, grow to 15 mm long and 8 mm wide, entire, tip obtuse, base attenuate, Red Purple 71B on both sides lightening toward the base.

*Calyx description.*—11 mm long and 10 mm wide, campanulate, 5 lobes each 5.5 mm long and 4 mm wide, overlapping slightly, ovate, entire, tips obtuse, sparsely glandular, color outside Greyed Red 185A, inside Greyed Green 148C.

*Pistil description.*—3 fused at base, each 14 mm long and 3 mm wide, ovary oval, 6 mm long and 3 mm wide, Yellow Green 152D; style 6 mm long and 1 mm wide, Yellow Green 152D, stigma Greyed Purple 187A.

*Stamen description.*—10 in number, 8 mm long, filaments 7.5 mm long, Red Purple 65D, anthers 1.5 mm long, Yellow White 158A; pollen White 155A.

*Bloom period.*—March to April in Canby, Oreg.

*Lastingness of bloom.*—Each flower lasts about a week.

*Fragrance.*—None.

Fruit: a capsule, none produced.

Seed: none produced.

Pest and diseases: *Bergenia* are troubled by snails and slugs. This variety has no known resistances.

I claim:

1. A new and distinct *Bergenia* plant as herein illustrated and described.

* * * * *